(12) United States Patent
Wong et al.

(10) Patent No.: US 7,938,980 B2
(45) Date of Patent: May 10, 2011

(54) CHEMICAL ETCHING COMPOSITION FOR THE PREPARATION OF 3-D NANO-STRUCTURES

(75) Inventors: Sean Wong, Karlsruhe (DE); Georg von Freymann, Karlsruhe (DE); Martin Wegener, Karlsruhe (DE); Geoffrey Alan Ozin, Toronto (CA)

(73) Assignee: Forschungszentrum Karlsruhe GmbH, Karlsruhe (DE)

( * ) Notice: Subject to any disclaimer, the term of this patent is extended or adjusted under 35 U.S.C. 154(b) by 808 days.

(21) Appl. No.: 11/978,225

(22) Filed: Oct. 26, 2007

(65) Prior Publication Data
US 2008/0128391 A1 Jun. 5, 2008

(30) Foreign Application Priority Data
Oct. 26, 2006 (EP) .................................... 06122987

(51) Int. Cl.
B44C 1/22 (2006.01)
C03C 15/00 (2006.01)
C03C 25/68 (2006.01)
C23F 1/00 (2006.01)
C25F 3/00 (2006.01)

(52) U.S. Cl. .......................................... 216/97; 216/87
(58) Field of Classification Search .................. 216/87, 216/97, 24
See application file for complete search history.

(56) References Cited

U.S. PATENT DOCUMENTS
4,405,710 A 9/1983 Balasubramanyam et al.

OTHER PUBLICATIONS

Zaharescu et al: "Effects of Some Secondary Amines on the Oxidation . . . " Barking GB, vol. 68, No. 1, Apr. 1, 2000, pp. 83-86, XP004294916.
Feigel et al: "Chalcogenide Glass-Based 1-12 Three-Dimensional . . . " Melville, NY, US, vol. 77, No. 20, Nov. 13, 2000, pp. 3221-3223.
Lodeiro et al: "Intramolecular Excimer Formation and Sensing Behavior . . . " Sensors and Actuators, ISSN: 0925-4005, Oct. 28, 2005, XP002435735.

*Primary Examiner* — Roberts Culbert
(74) *Attorney, Agent, or Firm* — Lucas & Mercanti, LLP; Klaus P. Stoffel

(57) ABSTRACT

A method of using a chemical compound as an etchant for the removal of unmodified areas of a chalcogenide-based glass, while leaving the imagewise modified areas un-removed, wherein the compound contains a secondary amine, R1 R2 NH, with R1 and/or R2 having a sterically bulky group with more than 5 atoms.

6 Claims, 3 Drawing Sheets

Experimentally determined etch rates and etch selectivities of the amines shown in figure 1.

Amines that have been synthesized.

Experimentally determined etch rates and etch selectivities of the amines shown in figure 1.

High-aspect ratio 3-D structures that are fabricated using the amine etchant.

CHEMICAL ETCHING COMPOSITION FOR THE PREPARATION OF 3-D NANO-STRUCTURES

BACKGROUND OF THE INVENTION

1. Field of the Invention

The present invention relates to the use of a chemical compound as an etchant for the removal of the unmodified areas of an imagewise modified chalcogenide based glass while leaving the modified areas un-removed. Further the present invention is directed to a method for the preparation of a free standing 3-D nano-structure by using the mentioned compound as well as to the compound.

2. Description of the Related Art

Chalcogenide glasses are materials that have at least one element in its chemical composition that belongs to group VI of the period table, namely the elements sulfur, selenium and tellurium. These chalcogenide glasses are able to be used as photo-resistive material.

A resist material is known as a material that can have its chemical behavior modified via the exposure to an external stimulus. This stimulus could be induced by photons, electrons or other types of energy beams.

One method to generate a photoinduced change in chalcogenide based glasses is the method of three-dimensional direct laser writing (3D-DLW). The method of 3-D DLW takes advantage of the fact that the method utilizes laser wavelengths that are below the bandgap of the photoresist material, so that one-photon absorption is negligible. What this means is that without focusing the laser radiation that is utilized, the beam can essentially pass through the material without being absorbed. However, if highly intense laser radiation is used, such as those generated from a femtosecond laser, and the laser beam is tightly focused into a very small spot, in the order of 200 nm, then the probability of the laser energy being absorbed via a two-photon process would likely occur. However, the absorption only occurs at the focus of the laser spot where the laser intensity is the highest, all other areas where the laser intensity is not focused will not be polymerized. This ability for the laser energy to be selectively absorbed in a three-dimensional space allows for the in-situ, or direct, generation of a three-dimensional image inside the photoresist. The images that are generated using the 3-D DLW method provide very tall, or thick, structures, with minimum feature sizes below 200 nm, directly inside the photoresist. To etch out, or reveal this structure then requires a highly selective chemical etchant that allows for the total removal of the unexposed areas, while leaving the exposed areas behind.

A liquid etchant is generally defined as a chemical solution that is able to controllably remove a solid material. When such an etchant is used in the field of resists, it has the meaning that it possesses the ability to controllably remove areas that have not been modified using an external stimulus, (ie. photons, electron beams, etc), over that of those areas that have been modified using an external stimulus, or vice versa. In the instance described in the following, the removal of the unmodified areas over that of the modified areas serves to provide a negative image of the laser-beam or photo-mask, therefore this etchant is a negative tone etchant.

Liquid etchants for chalcogenide glasses have been formulated to take advantage of the fact that there is a chemical difference that arises in chalcogenide-based glasses after exposure to an external stimulus. There are two main types of liquid etchants that are known in the scientific and patent literature which etch chalcogenide-based glasses. These two types mainly differ by the solvent systems that they employ. The first type are water-based (aqueous), and the second are organic solvent based etchants.

In the aqueous based etchants, the active component in their composition is usually an inorganic base which generates a basic condition (pH>7) using anions such as hydroxide, sulfides, sulfites, disulfides, amines and cyanides. The basic environment creates oxidizing conditions which oxidize the components in the chalcogenide glass into water-soluble species, and thereby dissolving them in the aqueous phase. Additives such as surfactants are also added to increase the selectivity of the etchant composition. It has been shown that etchants containing these species are able to etch chalcogenide-glasses with some selectivity but they have only been shown to be confined to etching very thin films with structures having a height of no more than 500 nm. This is due to the fact that the oxidizing conditions are so strong, that all of the material whether modified or not, will be completely removed after a short time.

In the organic based etchants, the active components in its composition is usually a short chain amine, C<5, that is dissolved in an organic solvent. These compositions have also been shown to reveal thin 2-D structures usually no more than 500 nm thick. The organic amine again acts as an oxidant to oxidize the species in the chalcogenide-based glasses. Only very thin structures are made because the oxidizing conditions are again so strong that all of the material is removed, and hence the reaction is essentially kinetically controlled.

It has been shown that the photosensitive V-VI semiconducting chalcogenide glass, As2S3, is also compatible with the 3-D DLW process. But the etching chemistry in As2S3 is not developed well enough to take full advantage of the precision placement of 3-D features, and sub-diffraction limit resolution, that the 3-D DLW method routinely achieves in organic photopolymers (Wong et al. Adv. Mater. (2006), 18, pg 265-269).

The problem that was noticed earlier on when fabricating 3-D structures on the nano-scale was that the demands on the etchant's selectivity ($\gamma$), becomes much greater than for 2-D structures. The selectivity of an etchant ($\gamma$), is defined as the ratio between the rate of the unexposed areas (Ku) and the rate of the removal of the exposed areas (Ke). Therefore, when developing As2S3 as a negative-tone photoresist, the unexposed areas should be removed as quickly as possible, while the exposed areas should remain as long as possible, so as to afford a large $\gamma$. A large $\gamma$ will allow thick structures with fine resolution to be produced.

The first demand on an etchant system that requires a large $\gamma$, stems from the fact that 3-D structures must be immersed for a longer period of time in the etchant to develop its structures. This is a result of the slower diffusion of liquid etchants through a more obstructed nano-porous structure. Another demand is due to the higher reaction rate on the areas that have already been developed by the etchant in 3-D structures. This is because the surface area of a porous 3-D structure is much larger than the surface area of a 2-D structure of the same volume. Therefore, the etch selectivity of the etchant that is employed to directly develop a 3-D structure, must be significantly higher in the 3-D case than the 2-D case. Currently available etchant studies found in the literature (A. Feigel et al. Applied Physics letters (2003), 83, pg 4480.) that deal with As2S3 as a photoresist, are only investigated to be applied to fabricate thin 2-D structures less than 500 nm in height. There, the etch selectivity requirements are much lower. Functional 3-D structures (such as 3-D PBG materials, or nano and micro-machines) often require structures with a height of 20 microns or more. Therefore, the demands placed on the etch selectivity of the etchant composition for direct 3-D fabrication of 3-D nano-structures are much greater.

SUMMARY OF THE INVENTION

Therefore, the etchants that are currently available fail greatly when they are employed to etch thick 3-D structures generated via 3-D DLW. This is because those compositions found in the open literature (S. A. Zenkin et al. Glass Physics and Chemistry (1997), 5, pg 393, A. Feigel et al. Applied Physics Letters, (2000) 77, pg 3221.) are used to etch thin 2-D structures, where the selectivity requirement is much lower. Accordingly an etchant composition that is tailored to fulfil the requirements of a highly selective etchant to etch thick 2-D and 3-D structures generated via 3-D DLW is required.

The present invention is directed to the use of a chemical compound as etchant for the removal of the un-modified areas of a chalcogenide-based glass while leaving the modified areas un-removed, wherein the compound contains a secondary amine R1R2NH with R1 and/or R2 having a sterically bulky group with more than 5 atoms.

The various features of novelty which characterize the invention are pointed out with particularity in the claims annexed to and forming a part of the disclosure. For a better understanding of the invention, its operating advantages, specific objects attained by its use, reference should be had to the drawing and descriptive matter in which there are illustrated and described preferred embodiments of the invention.

DESCRIPTION OF THE PREFERRED EMBODIMENTS

The invention that is presented here relates to an etching composition that contains a family of bulky organic secondary amine molecules, R1R2NH, which when used as the main component in an etchant, provides a high selectivity that is required to produce 2-D and 3-D etched articles using chalcogenide-based glasses. The ability of such an etchant described herein to provide a high etch selectivity rests entirely on the steric properties of the R groups of the secondary amine molecule itself. More specifically, the secondary amine molecule that is used here must have R groups containing 5 or more atoms. Such a molecule, when dissolved in an organic solvent, has the ability to selectively remove the un-modified areas of a chalcogenide based-glass while preventing the removal of the exposed areas of the chalcogenide-based photoresist. The use of such an etching composition allows thick, or tall, two- or three-dimensional articles to be fabricated from chalcogenide-based glasses using 3-D DLW.

Particularly R1 and R2 are most preferred but not limited to, benzyl-, napthyl-, pyrenyl-, pyridinyl-, isoamyl-, anthracyl-, and boranes. The atoms are preferably selected from the groups carbon, boron and nitrogen, in particular carbon.

In a most preferred form of the present invention, R is an aryl group.

Secondary amines containing at least one benzyl group are preferably used. Examples of advantageous secondary amines containing at least one benzyl group are dibenzylamine and N-(4-fluorobenyzl)-benzylamine.

Figure 1:
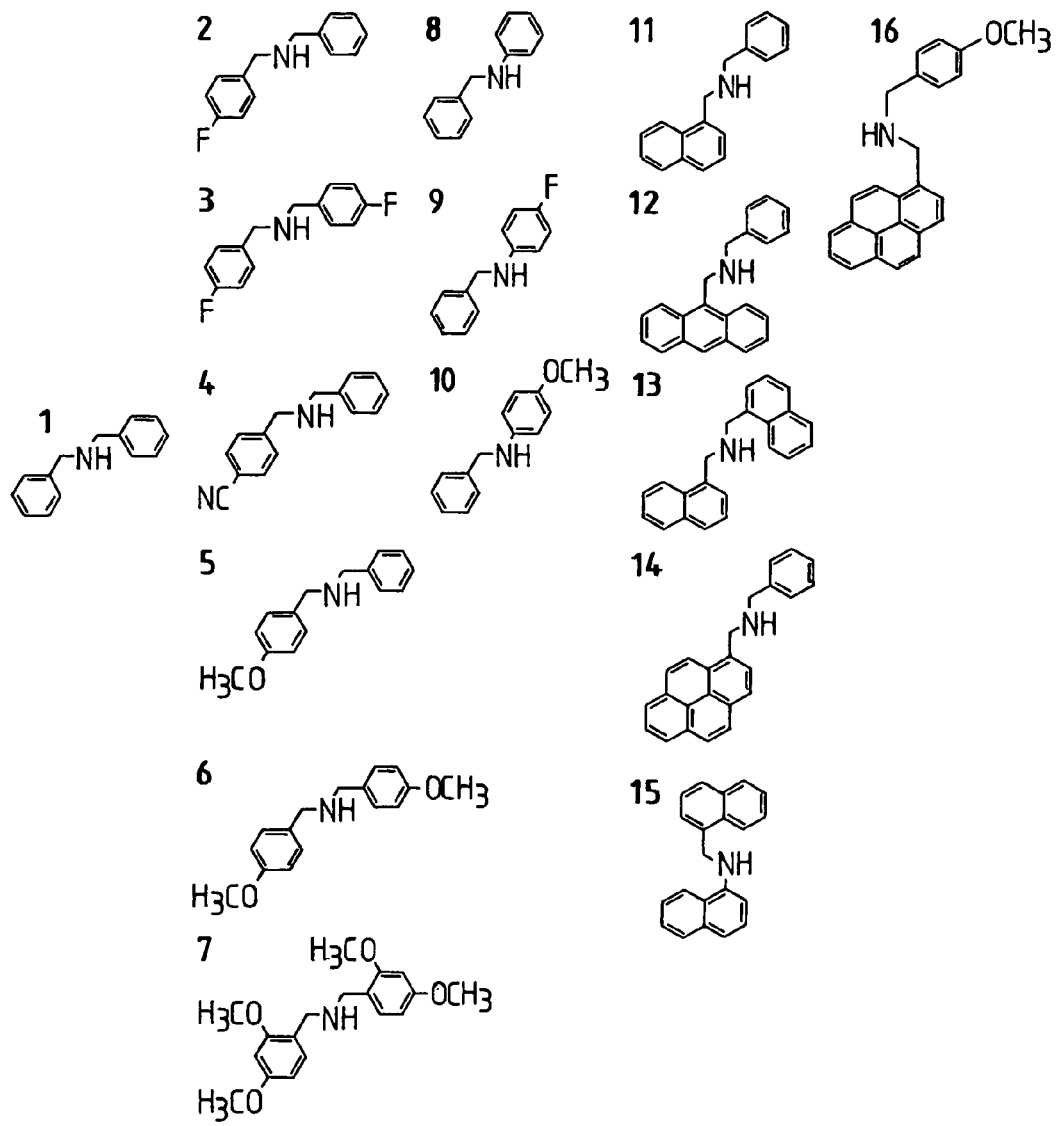
FIG. 1 shows amines that have been synthesized.
Figure 2:
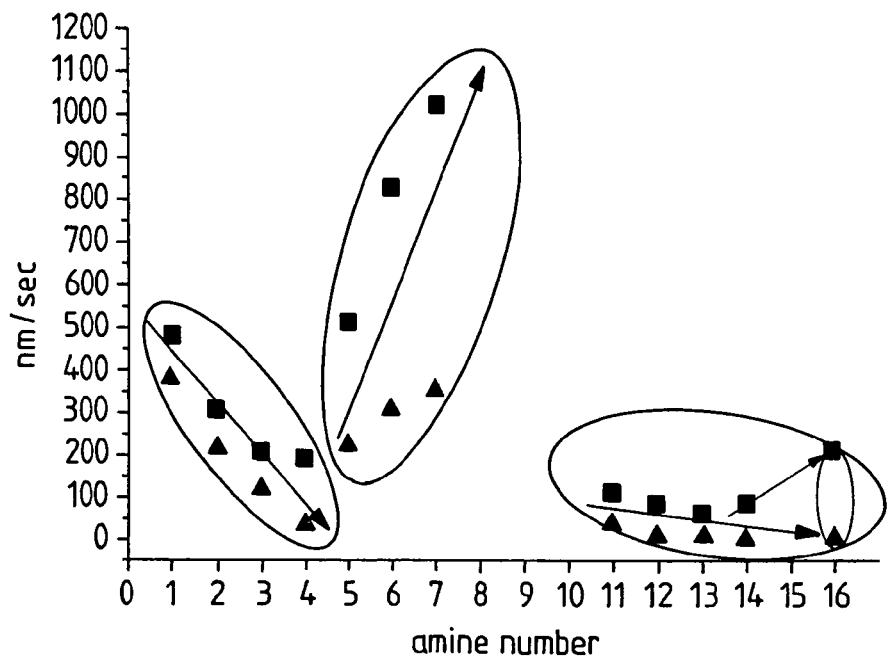
FIG. 2 shows experimentally determined etch rates and etch selectivities of the amines shown in FIG. 1.
Figure 2:
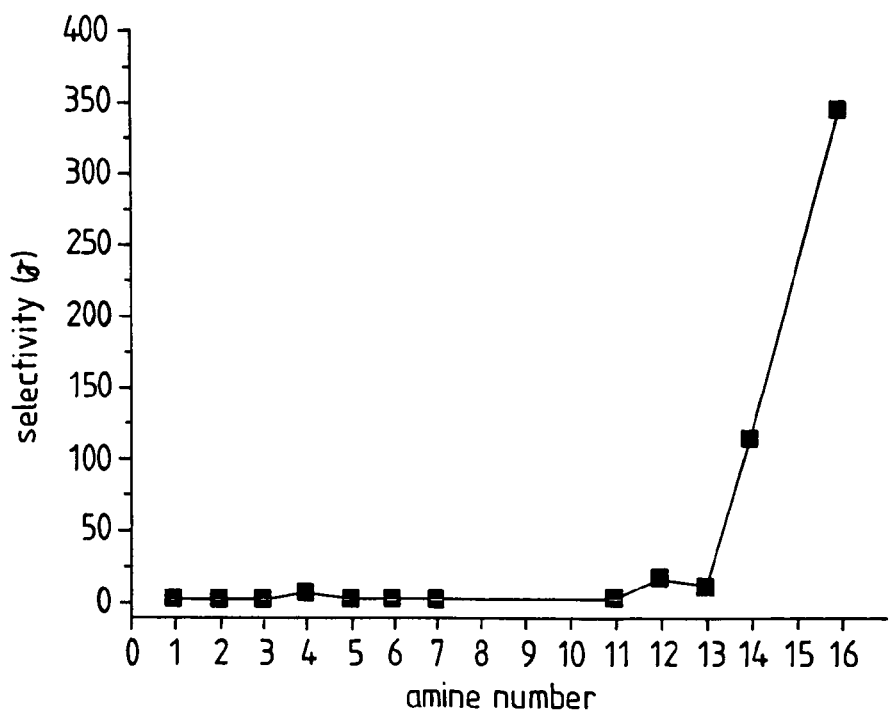

Examples of amines which can be used in the present invention are shown in FIG. 1.

Most preferably the chemical compound used in the present invention contains N-(4-methoxybenzyl)-(pyren-1-yl-methyl)amine or N-(benzyl)-(pyren-1-ylmethyl)amine.

The chemical compound according to the invention is preferably soluble in an organic solvent so as to form a liquid phase etchant.

The etch selectivity of the liquid etchant is preferably greater than 100 to 1, more preferably greater than 150 to 1.

Each chalcogenide glass used in the present invention have at least one element in its chemical composition that belongs to the group VI of the periodic table, preferably S, Se, Te, in particular S.

Further, the present invention is directed to a method for fabricating 3-D nano-structures consisting of chalcogenide glass. According to that method the glass has been 3-D dimensionally photo-patterned via 3-D DLW (Direct Laser Writing).

Thereafter the unmodified areas are removed. In the present invention the above mentioned compound is used as etchant.

Finally the present invention is directed to N-(4-methoxybenzyl)-(pyren-1-yl-methyl)amine and N-(benzyl)-(pyren-1-ylmethyl)amine. These substances are the preferred etchants of the present invention.

The present invention is explained in the following three examples:

Example 1

The chemical N-(4-methoxybenzyl)-(pyren-1-yl-methyl) amine, C16H9CH2NHCH2C6H5OCH3, is dissolved in a solution of 1.8 ml dimethylsulfoxide and 0.8 ml 1,2-dichloroethane at a concentration of 0.66 M (0.539 g). This solution is then mixed until it is homogenous and then it is poured into a shallow glass dish. The chalcogenide photoresist used here is arsenic trisulfide, As2S3, and it has been patterned in three-dimensions using the 3-D DLW method that was described in the earlier sections of this patent. The thickness of this photoresist is first measured and recorded using a fiber interferometer. The film is then placed gently inside this solution and the shallow dish is covered with a watch glass. The film, here about 10 microns thick, is left soaking in the etchant, at room temperature, undisturbed for about 47 minutes. At the end of this time, one can visually see that the unexposed area of the photoresist, which has an orange-yellow color, is completely removed. This represents a etch rate of the unexposed areas, Ku, of 210 nm/min. The film is taken out of the etchant and is rinsed with copious amount of acetone. The structures are then checked with a microscope.

Figure 3:
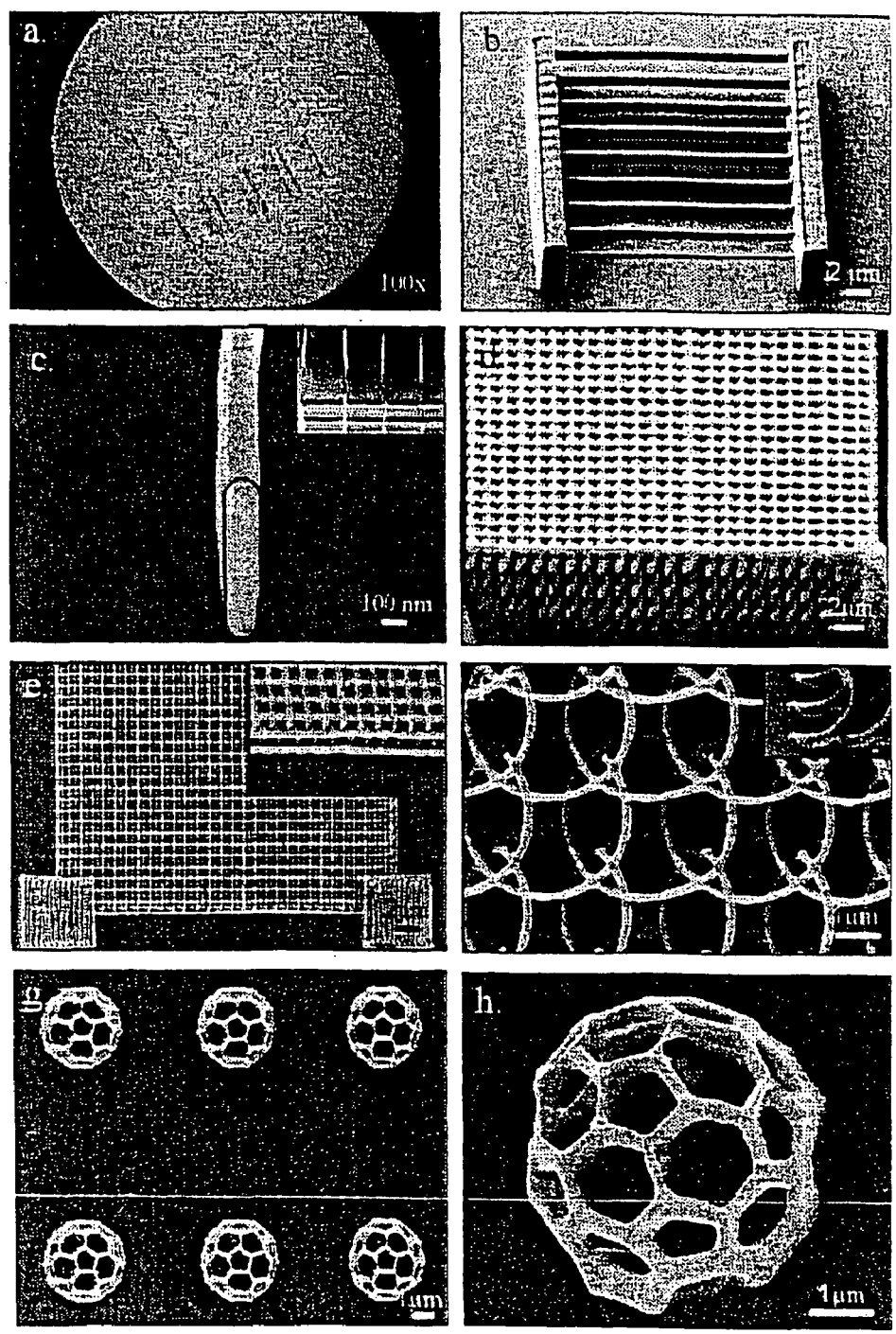
FIGS. 3a to 3h show high-aspect ratio 3-D structures that are fabricated using the amine etchant according to the invention.

The structure is then replaced into the etchant and is allowed to soak for 4 days or 5760 minutes. At the end of this time, the substrate with the structures are once again removed and rinsed with copious amounts of acetone and then placed under the microscope. FIG. 3a shows light microscope and scanning electron micrographs of the structure after 5760 minutes (FIGS. 3b and c), and they are essentially the same as at the time of 47 minutes. Therefore, theoretically, the etch rate is infinity. However for comparisons purposes, the time of 5760 minutes is taken as if the structures would have been totally removed. Hence the etch rate of the exposed area, Ke, for comparison purposes, is then 0.61 nm/min. Since the etch selectivity is the ratio of the Ku versus Ke, the etch selectivity in this case is at least 344 to 1.

Example 2

The chemical N-(benzyl)-(pyren-1-ylmethyl)amine, C6H6CH2NHCH2C16H9, is dissolved in a solution of 1.8 ml dimethylsulfoxide and 0.8 ml 1,2-dichloroethane at a concentration of 0.66 M (0.503 g). This solution is then mixed until it is homogenous and then it is poured into a shallow glass dish. The chalcogenide photoresist used here is arsenic trisulfide, As2S3, and it has been patterned in three-dimensions using the 3-D DLW method that was described in the earlier sections of this patent. The thickness of this photoresist is first measured and recorded using a fiber interferometer. The film is then placed gently inside this solution and the shallow dish is covered with a watch glass. The film, here about 10 microns thick, is left soaking in the etchant, at room temperature, undisturbed for about 102 minutes. At the end of this time, one can visually see that the unexposed area of the photoresist, which has an orange-yellow color, is completely removed. This represents a etch rate of the unexposed areas, Ku, of 98 nm/min. The film is taken out of the etchant and is rinsed with copious amount of acetone. The structures are then checked with a microscope.

The structure is then replaced into the etchant and is allowed to soak for 3 days or 4320 minutes. At the end of this time, the substrate with the structures are once again removed and rinsed with copious amounts of acetone and then placed under the microscope. FIG. 3a shows light microscope and scanning electron micrographs of the structure after 3 days, or 4320 minutes (FIGS. 3b and c), and they are essentially the same as at the time of 102 minutes. Therefore, theoretically, the etch rate is infinity. However for comparisons purposes, the time of 4320 minutes is taken as if the structures would have been totally removed. Hence the etch rate of the exposed area, Ke, for comparison purposes, is then 0.87 nm/min. Since the etch selectivity is the ratio of the Ku versus Ke, the etch selectivity in this case is 112 to 1.

All 16 secondary benzylamine derivatives containing at least one benzyl group (see FIG. 1) have been synthesized using a two-step synthesis. This consists of first forming an imine via the condensation coupling of an aldehyde and a primary amine, and then subsequently reducing the imine to obtain the final product.

To ensure that the same conditions for the comparison between the different secondary amines are used, the etching solutions are all prepared by dissolving the amine in a solvent system of dimethylsulfoxide (dmso) and 1,2-dichloroethane (1,2-dce) at a concentration of 0.66 M. We chose dmso as the solvent because it is a good solvent for SN2 type reactions. The addition of small amounts of 1,2-dce serves to aid in the salvation of the larger non-polar amine molecules. The ratio of the 2 solvents was adjusted so that the Hildebrand constant of the overall solution has a value of 23. The direct laser written film is then placed in the etchant and periodically removed to count the rungs of the resulting 3D-nanostructures in the form of ladders with rungs that remain. The rate of dissolution of the unexposed areas (Ku) is defined as the amount of time that is required to completely dissolve all of the unexposed photoresist. The rate of dissolution of the exposed area (Ke) is the amount of time that is required to remove the rungs of the ladders in the 3-D structure. The overall etch selectivity ($\gamma$) is then calculated as a ratio of these two etch rates (Ku/Ke).

FIGS. 3b to 3h show scanning electron micrographs of some examples of different free-standing 3-D nanostructures that one could fabricate using the amine (13), when used in the method as described in the patent. Image b, is the "step-ladder" test structure. Image c, is a close up of the cross-section of a single rung of the ladder structure. It shows that smallest feature that is definable using this system is on the order of 170 nm. Image d, is a 3-D array of spirals. Image e, is a 3-D woodpile photonic crystal. Image f, a 3-D array of fine spirals with individual feature sizes on the order of 170 nm. Image g, is an array of nano-soccer balls. Image h, is a close-up image of the soccer-ball. One should notice that the nanostructures produced using this material and method, possess exceptionally smooth and defect-free surfaces. Such aspects are critical for highly demanding applications of using nanostructures, such as those intended for optical applications.

On surveying the data tabulated in the following table, there is almost a 100 fold increase in the etch selectivity on synthetically exchanging one of the benzyl arm that is present in molecule (1) to a pyrenyl arm of (14).

TABLE

Summary of the etch selectivity ($\gamma$) and etch rate of all of the dibenzylamine derivatives synthesized.

| Amine identity | Ku (nm/min) | Ke (nm/min) | Selectivity ($\gamma$) |
|---|---|---|---|
| 1 | 476 | 379 | 1.26 |
| 2 | 306 | 212 | 1.44 |
| 3 | 207 | 114 | 1.81 |
| 4 | 188 | 30 | 6.27 |
| 5 | 513 | 219 | 2.34 |
| 6 | 826 | 304 | 2.72 |
| 7 | 1020 | 349 | 2.92 |
| 8 | No reaction | No reaction | — |
| 9 | No reaction | No reaction | — |
| 10 | No reaction | No reaction | — |
| 11 | 111 | 33 | 3.36 |
| 12 | 84.7 | 5.02 | 16.87 |
| 13 | 59.7 | 5.31 | 11.24 |
| 14 | 98 | 0.87 | 113.79 |
| 15 | No reaction | No reaction | — |
| 16 | 210 | 0.61 | 344.26 |
| triethylamine | No reaction | No reaction | — |

Further, etching can be performed by doubling the concentration of (13) to 1.32 M. The result is that the etch rate of the unpolymerized areas has increased from 85 nm/s to 170 nm/s, a two-fold increase in the rate, while the polymerized areas remain un-etched after 96 hours.

In molecule 13 both arms of the amine have been modified to napthyl-groups. Although the Ku has decreased as expected, the selectivity has not improved.

With regard to the novel amine, N-(4-methoxybenzyl)-(pyren-1-yl)amine (16) a high etch selectivity ($\gamma$=344) is obtained.

While specific embodiments of the invention have been described in detail to illustrate the inventive principles, it will be understood that the invention may be embodied otherwise without departing from such principles.

We claim:

1. A method of using a chemical compound as an etchant for a chalcogenide-based glass, comprising the steps of:
    removing unmodified areas of the chalcogenide-based glass by etching with N-(4-methoxybenzyl)-(pyren-1-yl-methyl)amine or N-(benzyl)-(pyren-1-ylmethyl) amine; and,
    leaving imagewise modified areas of the glass un-removed.

2. The method according to claim 1, wherein the glass composition contains S, Se and Te.

3. The method according to claim 1, comprising making the modified areas via imagewise exposure.

4. The method according to claim 1, wherein the glass composition is a photo-patterned photo-resist.

5. The method according to claim 1, comprising generating photoinduced changes in the chalcogenide glasses by 3-D dimensional direct laser writing.

6. A method of fabricating 3-D nano-structures consisting of chalcogenide glass, comprising the steps of:

three-dimensionally photo-patterning the glass via 3-D DLW; and, removing unmodified areas thereafter by using N-(4-methoxybenzyl)-(pyren-1-yl-methyl)amine or N-(benzyl)-(pyren-1-ylmethyl)amine as an etching agent.

* * * * *